United States Patent [19]

Yoshida et al.

[11] Patent Number: 5,475,126
[45] Date of Patent: Dec. 12, 1995

[54] BENZOPHENONE DERIVATIVE, AN ULTRAVIOLET LIGHT ABSORBENT AND AN ENDERMIC LINIMENT

[75] Inventors: Masashi Yoshida; Keiichi Uehara, both of Yokohama, Japan

[73] Assignee: Shiseido Company Ltd., Tokyo, Japan

[21] Appl. No.: 346,300

[22] Filed: Nov. 23, 1994

[30] Foreign Application Priority Data

Nov. 25, 1993 [JP] Japan .................................. 5-319068

[51] Int. Cl.$^6$ .................................................. C07F 7/08
[52] U.S. Cl. ............................ 556/439; 424/59; 424/401
[58] Field of Search .............................. 556/439; 424/59, 424/401; 514/844, 845

[56] References Cited

U.S. PATENT DOCUMENTS

| | | | |
|---|---|---|---|
| 2,938,047 | 5/1960 | Black | 556/439 |
| 5,118,839 | 6/1992 | Eisenbraun et al. | 556/439 U X |
| 5,254,542 | 10/1993 | Sakuta et al. | 556/439 U X |
| 5,270,426 | 12/1993 | Sakuta et al. | 556/439 U X |

FOREIGN PATENT DOCUMENTS

| | | |
|---|---|---|
| 2657351 | 1/1991 | France . |
| 04217622 | 10/1990 | Japan . |
| 9310745 | 12/1991 | WIPO . |

*Primary Examiner*—Paul F. Shaver
*Attorney, Agent, or Firm*—Townsend & Banta

[57] ABSTRACT

A silicone-type benzophenone derivative represented by Formula 1 below, an ultraviolet light absorbent and an endermic liniment which contains it.

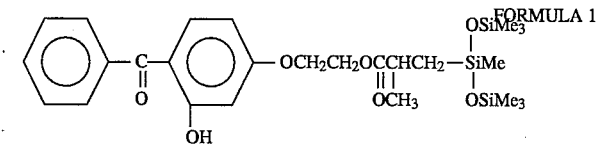

FORMULA 1

The silicone-type benzophenone derivative of the present invention exhibits a superior ability to absorb UV-A and UV-B and is compatible with silicone-type bases.

3 Claims, 1 Drawing Sheet

BENZOPHENONE DERIVATIVE, AN ULTRAVIOLET LIGHT ABSORBENT AND AN ENDERMIC LINIMENT

FIELD OF THE INVENTION

The present invention relates to a new silicone-type benzophenone derivative as well as an ultraviolet light absorbent and an endermic liniment using same, and more particularly to a new silicone-type benzophenone derivative which highly dissolves in silicone oil, has superior water resistance and oil resistance, and also has ultraviolet light absorption characteristics with an absorption wavelength in the UV-AB region.

BACKGROUND OF THE INVENTION

Ultraviolet light is known to cause various changes in skin. In dermatology, the wavelength spectrum is divided into the long wavelength ultraviolet light region, i.e. 400–320 nm, the medium wavelength ultraviolet light region, i.e. 320–290 nm, and the short wavelength ultraviolet light region, i.e. 290 nm or less. These regions are referred to as UV-A, UV-B and UV-C, respectively.

Usually, most of the ultraviolet light which people are exposed to is from sunlight. The part of the ultraviolet light which reaches the earth comprises UV-A and UV-B, while UV-C is absorbed by the ozone layer and very little of it reaches the earth. Of the ultraviolet light which reaches the earth, UV-B is known to cause erythema and blisters and accelerate formation of melanin when the skin is irradiated by more than a certain quantity, while UV-A is known to darken the skin immediately after the irradiation and also to enhance the skin-degradating action of UV-B. UV-A is important in terms of prevention of the development and aggravation of liver spots and freckles.

However, research on the action of UV-A on the skin started relatively recently, and only dibenzoylmethane derivatives are known as UV-A absorbents. Benzophenone derivatives are known as UV-AB absorbents which have absorption bands covering both UV-A and UV-B regions.

For the base for endermic liniments, silicone-type bases such as dimethylpolysiloxane are widely used. This is largely because the silicone-type bases are easy to use, i.e. they spread well, give a refreshing feeling and are not sticky, and also because of their superior functioning, i.e. they are not washed away easily by perspiration or water.

Flowever, the existing UV-A, UV-B and UV-AB absorbents have very low compatibility with the silicone-type bases. Therefore, in order to blend them into an endermic liniment with the silicone-type bases, it was necessary to add an oil base. This made it difficult to fully utilize the advantages of the silicone-type bases described above.

Due to this problem, development of an ultraviolet absorbent which is soluble in silicone oil and superior in terms of water resistance and oil resistance, and at the same time gives sufficient protection against ultraviolet light, has been strongly desired.

SUMMARY OF THE INVENTION

The inventors had discovered a silicone-type cinnamic acid derivative(s) which was a highly safe UV-B absorbent with a high solubility in silicone oil and superior water resistance and oil resistance, and filed a patent application for it (Japanese application Serial No. Tokogan Sho 63-168838). The inventors carried out further research for the purpose of obtaining an ultraviolet light absorbent (UV-AB absorbent) with a high solubility in silicone oil and superior water resistance and oil resistance as well as an appropriate UV-AB wavelength region, and discovered that the silicone-type benzophenone derivative(s) of the present invention have the desired aforementioned characteristics.

That is, the silicone-type benzophenone derivative and the ultraviolet light absorbent of the present invention are represented by the following Formula 2:

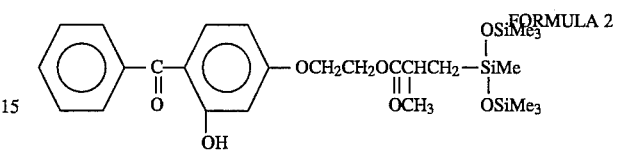

FORMULA 2

According to the present invention, an excellent endermic liniment contains said silicone-type benzophenone derivative.

Figure 1:
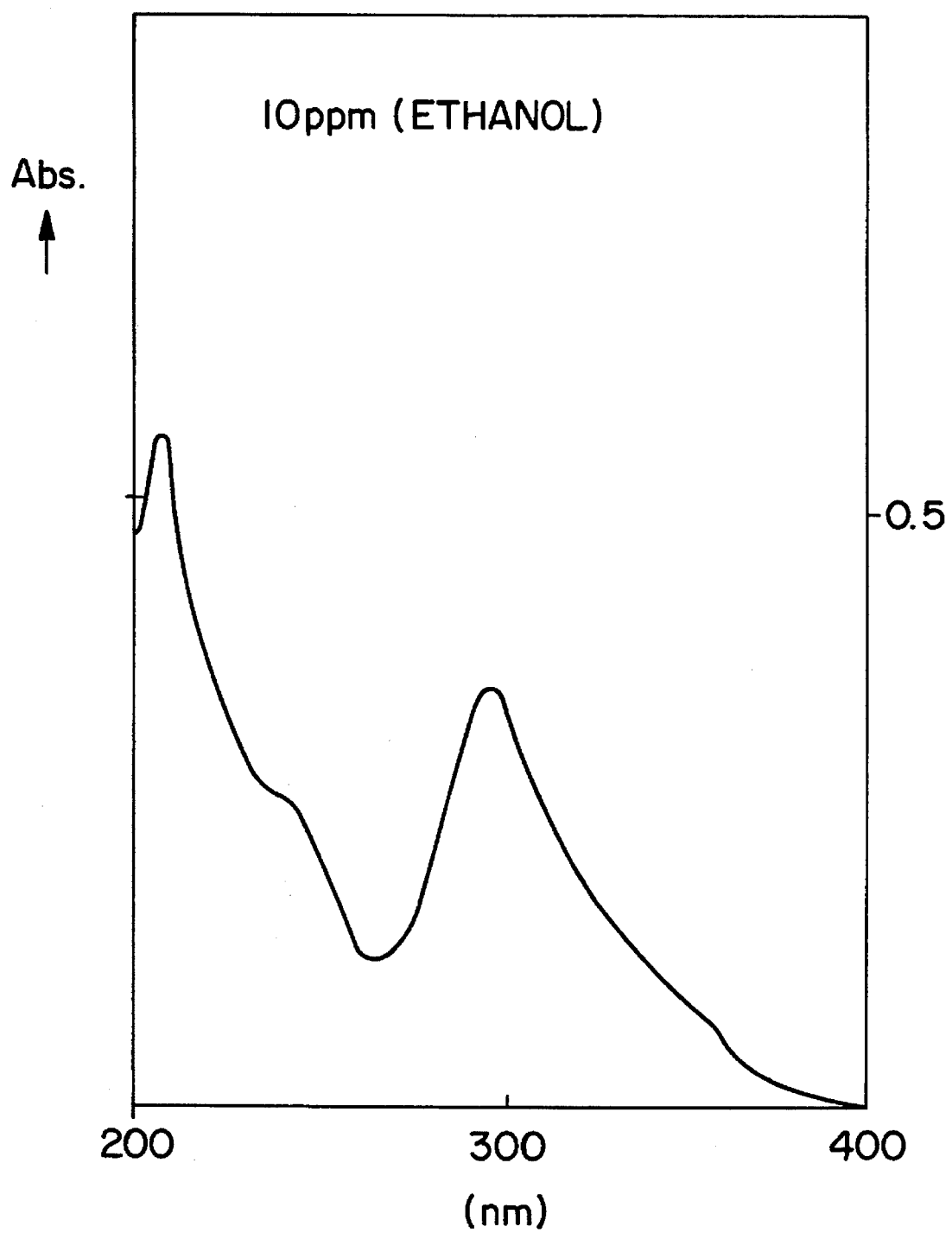
FIG. 1 is an ultraviolet absorption spectrum of the compound of Formula 2 in an ethanol solvent according to the present invention.

The details of the present invention are described below.

DETAILED DESCRIPTION OF THE INVENTION

The silicone-type benzophenone derivative according to the present invention can be synthesized by a conventional hydrosilylation reaction using a corresponding benzophenone derivative.

That is, the corresponding benzophenone derivative, 1,1,1,3,5,5,5-heptamethyltrisiloxane and a conventional catalyst, such as a rhodium complex, a platinum complex with an unsaturated compound, chloro-platinic acid and a platinum complex carried by carbon, are reacted in an organic solvent such as toluene, xylene or hexane under atmospheric pressure at 50° C. or a temperature lower than the boiling point of the solvent until the Si—H groups are gone to obtain the silicone-type benzophenone derivative of the present invention.

While the ultraviolet light absorbent of the present invention was developed as described above, its applications are not particularly limited and it can be used in various products which use ultraviolet light absorbents depending on the characteristics and purposes of the silicone-type benzophenone derivative.

The endermic liniment of the present invention is not particularly limited in its applications and it can be used for cosmetics, quasi drugs and such, depending on the characteristics and purposes of the silicone-type benzophenone derivative.

For the base for blending said silicone-type benzophenone derivative into endermic liniments such as cosmetics and quasi drugs, anything it dissolves in can be used. Silicone oil bases are particularly easy to use, i.e. they spread well, give a refreshing feeling and are not sticky, and also they have superior functioning, i.e. they are highly water resistant and are not washed away easily by perspiration or water.

The following components which are commonly used can also be blended into the endermic liniment of the present invention: powders including inorganic powders such as talc, kaolin and mica, organic powders such as nylon, polyethylene and silicone, inorganic pigments such as titanium dioxide and iron oxide and organic pigments; liquid fat and oils including olive oil, jojoba oil, macademia nut oil and triglyceride; waxes including carnauba wax, bees wax, candelilla wax and lanolin; hydrocarbons including liquid paraffin, ceresin and squalene; oily components including silicone oil and fluorine-containing oil; resins including silicone resin and flurorine-containing oil; thickeners including xanthangum, carrageenan, methyl cellulose, carboxyvinylpolymer, polyvinyl alcohol, bentonite and aluminum magnesium silicate; moisture-retaining agents including glycerine, polyethyleneglycol and hyaluronic acid; lubricants; ultraviolet light absorbents other than the present invention; antioxidants; surface active agents including cationic surface active agents, anionic surface active agents, nonionic surface active agents and amphoteric surface active agents; preservatives; perfumes; water; alcohol; polymers; sequestering agents; pH adjusting agents; drugs, etc.

Any formulation can be used for the endermic liniment of the present invention, i.e. it can take any form including powder, cream, paste, stick, liquid, spray and foundation. It can also be emulsified using an emulsifier to make the water in oil type or oil in water type.

The blend ratio of the compound of the present invention is, depending on the formulation as mentioned above, 0.1–20 wt % in general, and preferably 0.5–10 wt %.

EXAMPLES

Details of the present invention are described below by showing synthesis examples of the silicone-type benzophenone derivative of the present invention and its physico-chemical properties. The present invention is not limited to these examples.

Synthesis Example 2.79 g of a benzophenone derivative (1) and 1,1,1,3,5,5,5-heptamethyltrisiloxane (hereafter abbreviated as "MHM") (2) were dissolved in 100 ml of toluene, and chloro-platinic acid was added as a catalyst. The mixture was heated and stirred at the refluxing temperature for 3 hours. After completion of the reaction, a conventional treatment was conducted and, by means of silica gel column chromatography (silica gel C-300, toluene eluent), 5.52 g of the target compound, the silicone-type benzophenone derivative represented by Formula 2, was obtained (yield 50.9%). It was in a colorless liquid form.

The reaction formula is shown below in Formula 3.

FORMULA 3

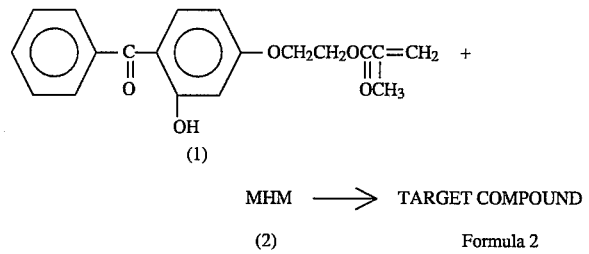

MHM $\longrightarrow$ TARGET COMPOUND (2)  Formula 2

The compound was identified using the following analytic values: $^1$H-NMR (CDCl$_3$) 12.60 (1H, OH, s), 7.50 (6H, arom., m), 6.50 (1H, arom., s), 6.40 (1H, arom., d), 4.40 (2H, CH2, t), 4.20 (2H, CH2, t), 2.57 (1H, <u>CH</u> (Me), m), 1.18 (3H, CH (<u>Me</u>), d), 0.80 (2H, CH2, m), −0.01 (18H, OSiMe3×2, s), −0.05 (3H, SiMe, s)

A UV absorption spectrum in ethanol is shown in FIG. 1.

As shown above, the silicone-type benzophenone derivative according to the present invention has a superior absorption in the UV-AB wavelength region.

As for solubility in a silicone base, the solubility testing in dimethylpolysiloxane and methylphenylpolysiloxane was conducted at 25° C.

In both cases, 50 wt % or more dissolved, indicating an excellent solubility. On the other hand, 2-hydroxybenzophenone, which has a similar structure, was hardly soluble at all.

As for the water resistance and oil resistance, the silicone-type benzophenone derivative of the present invention was mixed in water, 50% ethanol and oil, such as liquid paraffin, followed by agitation. The mixtures were then let stand for 60 days at 50° C. No hydrolysis or such was observed, indicating excellent water resistance and oil resistance.

The silicone-type benzophenone derivative of the present invention does not have any problems in terms of safety regarding sensitization, mutagenicity, photo-sensitization and photo-toxicity, and is safe under heat (including hydrolysis). For stability against light, it is completely stable when irradiated by normal sunlight, and thus is an excellent UV-AB absorbent.

Examples and comparative examples for using the silicone-type benzophenone derivative of the present invention as an ultraviolet light absorbent are shown below to further describe the present invention. The present invention is not limited to these examples. The blend ratio is expressed in wt % units.

Example 1

Sunscreen (oil type)

| | |
|---|---|
| (1) decamethylcyclopentasiloxane | 48.0% |
| (2) dimethylpolysiloxane (10 CS/25° C.) | 20.0 |
| (3) methylphenylpolysiloxane (20 CS/25° C.) | 20.0 |
| (4) silicone resin | 10.0 |
| (5) silicone-type benzophenone derivative (Formula 2, same as below) | 2.0 |

Preparation Method:
(1) through (5) are mixed, dissolved thoroughly, and filtered to obtain the product.

Comparative Example 1
The product was obtained in the same manner as in Example 1 except for the fact that (5) was excluded.

Example 2

Sunscreen (W/O cream)

| | |
|---|---|
| (1) Octamethylcyclopentasiloxane | 28.0% |
| (2) dimethylpolysiloxane (100 CS/25° C.) | 5.0 |
| (3) dimethylpolysiloxane (2,500,000 CS/25° C.) | 3.0 |
| (4) Liquid paraffin | 5.0 |
| (5) Silicone-type benzophenone derivative (same as in Example 1) | 1.5 |
| (6) Polyether modified silicone (400 CS/25° C.) (Polyoxyethylene content 20 wt %) | 6.0 |
| (7) Purified water | 43.1 |

-continued

|   |   |
|---|---|
| (8) L-sodium glutamate | 3.0 |
| (9) 1,3-butyleneglycol | 5.0 |
| (10) Preservative | 0.2 |
| (11) Perfume | 0.2 |

Preparation Method:

(1) through (6) and (11) are mixed, heated, dissolved and the temperature of the mixture is maintained at 70° C. to obtain the oil phase. Separately, (7) through (10) are heated, dissolved and the temperature of the mixture is maintained at 70° C. to obtain the water phase. The water phase is added to the oil phase and the resulting mixture is thoroughly emulsified by an emulsifier. The emulsified product is agitated while being cooled. When the temperature is 35° C. or lower, the product is poured into a container and let stand until hard.

Comparative Example 2

The product was obtained in the same manner as in Example 2 except for the fact that (5) was excluded.

Example 3

Sunscreen (O/W cream)

|   |   |
|---|---|
| (1) Octamethylcyclopentasiloxane | 9.0% |
| (2) Liquid paraffin | 3.0 |
| (3) Isopropylmyristate | 2.0 |
| (4) Vaseline | 5.0 |
| (5) Cetanol | 5.0 |
| (6) Stearic acid | 3.0 |
| (7) Glycerinemonoisostearate | 3.0 |
| (8) Silicone-type benzophenone derivative (same as in Example 1) | 0.1 |
| (9) Preservative | 0.2 |
| (10) Perfume | 0.2 |
| (11) Glycerine | 10.0 |
| (12) Propyleneglycol | 5.0 |
| (13) hyaluronic acid | 0.01 |
| (14) Potassium hydroxide | 0.2 |
| (15) Purified water | 54.29 |

Preparation Method:

(1) through (10) are heated and agitated at 70° C. to obtain the oil phase. (11) through (15) are heated to 70° C. and dissolved to obtain the water phase. The oil phase is added to the water phase and the resulting mixture is emulsified by an emulsifier. The emulsified product is cooled using a heat exchanger down to 30° C. and dispensed into a container to obtain the product.

Comparative Example 3

The product was obtained in the same manner as in Example 3 except for the fact that (8) was excluded.

Example 4

Sunscreen lotion

|   |   |
|---|---|
| (1) dimethylpolysiloxane (5 CS/25° C.) | 10.0% |
| (2) methylphenylpolysiloxane | 7.0 |
| (3) Stearic acid | 1.0 |
| (4) Silicone-type benzophenone derivative (same as in Example 1) | 20.0 |
| (5) Preservative | 0.2 |

-continued

|   |   |
|---|---|
| (6) Perfume | 0.2 |
| (7) Glycerine | 10.0 |
| (8) Montmorillonite | 0.5 |
| (9) Potassium hydroxide | 0.2 |
| (10) Purified water | 55.9 |

Preparation Method:

(1) through (6) are heated and agitated at 70° C. to obtain the oil phase. (7) through (10) are heated to 70° C. and dissolved to obtain the water phase. The oil phase is added to the water phase and the resulting mixture is emulsified by an emulsifier. The emulsified product is cooled down to 30° C. using a heat exchanger and dispensed into a container to obtain the sunscreen lotion.

Comparative Example 4

The product was obtained in the same manner as in Example 4 except for the fact that (4) was excluded.

The ultraviolet light blocking effect was measured for Examples 1–4 and Comparative Examples 1–4 obtained as described above.

The ultraviolet light blocking effect was measured using the ultraviolet light sensitive composition described below.

The ultraviolet light blocking effect was measured using the ultraviolet light sensitive composition described in Japanese unexamined patent publication (Tokkai) Sho 62-112020.

The process of preparing the ultraviolet light sensitive composition is described below.

A solution comprising 1.0 g of leuco crystal violet, 10 g of tetrabromodimethylsulfone, 10 g of ethylene-vinyl acetate copolymer and 100 ml of toluene is prepared and used as "solution I". Separately, a solution comprising 7 g of N,N-dimethylparaamino-2-ethylhexyl benzoate, 10 g of ethylene-vinyl acetate copolymer and 100 ml of toluene is prepared and used as "solution II".

First, Solution I is applied on a sheet of photographic base paper and dried such that the density is 1 g/m2 solid. On top of this, Solution II is applied such that the density is 5 g/m2 solid to obtain the ultraviolet light sensitive composition.

This ultraviolet light sensitive composition is a sheet of paper which changes its color from white to light purple to purple to deep purple as the quantity of the ultraviolet light it has been exposed to increases. 40 mg of the sample to be measured is mixed in castor oil and uniformly dispersed using a roller. A transparent PET film is placed on top of a round piece of said ultraviolet light sensitive composition with a 5 cm diameter, and 1.5 g of the mixture is applied on it such that the thickness is uniform. This is irradiated by an ultraviolet light source for 8 minutes and the PET with the sample on it is removed. A Hitachi spectrophotometer is used to measure the color of the ultraviolet light sensitive composition which has been irradiated with the ultraviolet light. The color difference is calculated by means of the LAB coordinates method with the color of the composition with zero ultraviolet dosage as the reference.

The results are shown in Table 1.

TABLE 1

|   | Color difference |
|---|---|
| Example 1 | 23 |

TABLE 1-continued

|  | Color difference |
| --- | --- |
| Comparative Example 1 | 58 |
| Example 2 | 36 |
| Comparative Example 2 | 45 |
| Example 3 | 40 |
| Comparative Example 3 | 57 |
| Example 4 | 30 |
| Comparative Example 4 | 52 |

As shown in Table 1, the color differences for the Examples are smaller than the color differences for the Comparative Examples, indicating a higher ultraviolet blocking effect. This means that a superior ultraviolet light blocking effect can be obtained by blending the silicone-type benzophenone derivative of the present invention.

Example 5

Dual purpose foundation

| (1) Silicone-treated titanium oxide | 9.5% |
| --- | --- |
| (2) Silicone-treated mica | 40.0 |
| (3) Silicone-treated talc | 20.45 |
| (4) Silicone-treated iron oxide | 7.5 |
| (5) Spherical nylon powder | 10.0 |
| (6) Trimethylolpropanetriisostearate | 5.0 |
| (7) Squalene | 3.0 |
| (8) Bees wax | 2.0 |
| (9) Silicone-type benzophenone derivative (Same as in Example 1) | 0.5 |
| (10) Sorbitan trioleate | 1.0 |
| (11) Preservative | 0.5 |
| (12) Vitamin E | 0.05 |
| (13) Perfume | 0.5 |

Preparation Method:

(1) through (5) were mixed with a Henshell mixer, and a heated and dissolved mixture of (6) through (13) were added to it, followed by mixing. The mixture was then crushed and molded on a mid-size plate to obtain a sunscreen dual purpose foundation.

Example 5 spread lightly, gave a natural finish and had a long lasting cosmetic effect and ultraviolet light blocking effect.

Example 6

Stick cosmetic

| (1) Titanium oxide | 10.0% |
| --- | --- |
| (2) Zinc oxide | 7.0 |
| (3) Mica | 16.0 |
| (4) Red iron oxide | 1.5 |
| (5) Yellow iron oxide | 1.5 |
| (6) Black iron oxide | 1.0 |
| (7) Dimethylpolysiloxane (20 CS/25° C.) | 29.4 |
| (8) Trimethylolpropanetri-2-ethylhexanoate | 10.0 |
| (9) Liquid paraffin | 8.0 |
| (10) Microcrystalline wax | 2.0 |
| (11) Ceresin | 1.0 |
| (12) Solid paraffin | 6.0 |
| (13) Silicone-type benzophenone derivative (Same as in Example 1) | 5.0 |
| (14) Perfume | 0.5 |
| (15) Antioxidant | 0.1 |
| (16) Sorbitan sesquioleate | 1.0 |

Preparation Method:

(1) through (6) were mixed with a Henshell mixer, and this mixture was added to a heated, stirred and dissolved mixture of (7) through (9), (13), (15) and (16), followed by mixing. A melted mixture of (10) through (12) and (14) was added to said mixture. After being thoroughly mixed, the product was molded into a stick form to obtain a sunscreen stick cosmetic.

Example 6 blocked ultraviolet light highly effectively, and had a long lasting cosmetic effect.

Example 7

Pre-Makeup

| (1) dimethylpolysiloxane (2 CS/25° C.) | 19.0% |
| --- | --- |
| (2) Glyceryltriisostearate | 10.0 |
| (3) isopropyl alcohol (registered trademark "Isopa") G | 5.0 |
| (4) Sorbitan sesquioleate | 1.0 |
| (5) Polyoxyethylene modified organo polysiloxane | 3.0 |
| (6) Purified water | 46.0 |
| (7) 1,3-butyleneglycol | 5.0 |
| (8) Titanium oxide fine particles | 10.0 |
| (9) Silicone-type benzophenone derivative (Same as in Example 1) | 5.0 |
| (10) Preservative | Appropriate amount |
| (11) Antioxidant | Appropriate amount |
| (12) Perfume | Appropriate amount |

Preparation Method:

(1) through (5), (9), (11) and (12) were stirred and dissolved at 70° C., and (6) through (8) and (10), already heated to 70° C., were added to this mixture. The product was emulsified and dispersed, and then cooled to obtain the target sunscreen pre-makeup.

Example 7 blocked ultraviolet light highly effectively, and had a long lasting cosmetic effect.

Example 8

Stick cosmetic

| (1) Titanium oxide | 10.0% |
| --- | --- |
| (2) Zinc oxide | 7.0 |
| (3) Mica | 16.0 |
| (4) Red iron oxide | 1.5 |
| (5) Yellow iron oxide | 1.5 |
| (6) Black iron oxide | 1.0 |
| (7) Dimethylpolysiloxane (20 CS/25° C.) | 26.4 |
| (8) Trimethylolpropanetri-2-ethylhexanoate | 8.0 |
| (9) Liquid paraffin | 8.0 |
| (10) Microcrystalline wax | 2.0 |
| (11) Ceresin | 1.0 |
| (12) Solid paraffin | 6.0 |
| (13) Silicone-type benzophenone derivative (Same as in Example 1) | 10.0 |
| (14) Perfume | 0.5 |
| (15) Antioxidant | 0.1 |
| (16) Sorbitan sesquioleate | 1.0 |

Preparation Method:

(1) through (6) are mixed with a Henshell mixer, and this mixture was added to a heated, stirred and dissolved mixture of (7) through (9), (13), (15) and (16), followed by mixing. A melted mixture of (10) through (12) and (14) was added to said mixture. After being thoroughly mixed, the product was molded into a stick form to obtain a sunscreen stick cosmetic. Example 8 blocked ultraviolet light even more efficiently than Example 6, and also had a long lasting cosmetic effect.

Example 9

Powdery foundation

| (1) Talc | 27.7 |
|---|---|
| (2) Mica | 30.0 |
| (3) Kaolin | 5.0 |
| (4) Titanium dioxide | 10.0 |
| (5) Mica titanium | 3.0 |
| (6) Zinc stearate | 1.0 |
| (7) Red iron oxide | 1.0 |
| (8) Yellow iron oxide | 3.0 |
| (9) Black iron oxide | 0.2 |
| (10) Polymethylsesquioxane powder | 5.0 |
| (11) Squalene | 6.0 |
| (12) Silicone-type benzophenone derivative (Same as in Example 1) | 5.0 |
| (13) Octyldodecylmyristate | 2.0 |
| (14) Sorbitan monooleate | 0.5 |
| (15) Perfume | 0.5 |
| (16) Antioxidant | 0.1 |

Preparation Method:

(1) through (10) are mixed with a Henshell mixer, and a heated and dissolved mixture of (11) through (16) is added to this, followed by mixing. The resulting mixture is crushed and molded on a mid-size plate to obtain a powdery foundation. This product blocked ultraviolet light highly effectively, and had a long lasting cosmetic effect.

The silicone-type benzophenone derivative of the present invention is a very useful new compound which absorbs light in the UV-AB wavelength region and dissolves well in silicone oils.

The ultraviolet light absorbent according to the present invention is particularly suitable for blending in endermic liniments such as cosmetics and quasi-drugs. Depending on the purpose, any amount of it can be blended in without compromising the characteristics of the base. This ultraviolet light absorbent also exhibits superior water resistance and oil resistance.

The endermic liniment which contains the silicone-type benzophenone derivative of the present invention is excellent because it can use a silicone-type base and is highly effective in blocking ultraviolet light.

An ultraviolet absorption spectrum of the compound (Formula 2) according to the present invention.

What is claimed is:

1. A silicone-type benzophenone derivative represented by the following Formula 1:

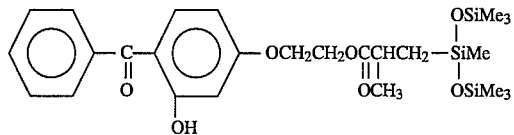

2. An ultraviolet light absorbent comprising the silicone-type benzophenone derivative of claim 1 and an effective carrier.

3. An endermic liniment comprising the silicone-type benzophenone derivative of claim 1 and an effective carrier.

* * * * *